United States Patent [19]

Stinski

[11] Patent Number: 5,180,813
[45] Date of Patent: Jan. 19, 1993

[54] EARLY ENVELOPE GLYCOPROTEIN OF HUMAN CYTOMEGALOVIRUS (HMCV) AND MONOCLONAL ANTIBODIES TO THE GLYCOPROTEINS

[75] Inventor: Mark F. Stinski, North Liberty, Iowa

[73] Assignee: University of Iowa Research Foundation, Iowa City, Iowa

[21] Appl. No.: 328,227

[22] Filed: Mar. 24, 1989

[51] Int. Cl.$^5$ .................. C07K 15/28; C07K 15/14
[52] U.S. Cl. .................. 530/388.3; 530/389.4; 530/395; 435/70.21; 435/172.2; 435/240.27; 424/86; 424/89
[58] Field of Search .................. 424/85.8, 86, 88, 89; 435/7.9, 70.21, 172.2, 240.27; 436/542; 530/387, 388, 395, 388.3, 389.4

[56] References Cited

U.S. PATENT DOCUMENTS

| | | | |
|---|---|---|---|
| 3,959,466 | 5/1976 | Plotkin | 424/89 |
| 4,689,255 | 8/1987 | Pereira | 424/89 |
| 4,716,104 | 12/1987 | Harris et al. | 435/5 |
| 4,743,562 | 5/1988 | Rasmussen et al. | 436/518 |
| 4,783,399 | 11/1988 | Oldstone et al. | 435/5 |

FOREIGN PATENT DOCUMENTS

| | | |
|---|---|---|
| 0173177 | 3/1986 | European Pat. Off. |
| 0180288 | 5/1986 | European Pat. Off. |
| 0236145 | 9/1987 | European Pat. Off. |
| 0268014 | 5/1988 | European Pat. Off. |
| 0277773 | 8/1988 | European Pat. Off. |
| 3619720 | 12/1987 | Fed. Rep. of Germany |

OTHER PUBLICATIONS

Stinski, M. F., "Synthesis of Proteins and Glycoproteins in Cells Infected with Human Cytomegalovirus", *J. Virol* 23:751-767, 1977.
Kouzarides, et al., "An Immediate Early Gene of Human Cytomegalovirus Encodes a Potential Membrane Glycoprotein", *Virology* 165:151-164, 1988.
Luckow et al., "Trends in the Development of Baculovirus Expression Vectors", *Biotechnology* 6:47-55, 1988.
Kipps et al. "Schemata for the Production of Monoclonal Antibody-Producing Aybridomes", in *Handbook of Experimental Immunology*, 4th ed., Weir et al., eds, Blackwell Scientific, 1986.
Chang et al., "A Human Cytomegalovirus Early Gene Has Three Inducible Promoters That Are Regulated Differently at Various Times After Infection", *J. Virology* 63(1):281-290, Jan. 1989.
Chang et al., "Identification and Expression of a Human Cytomegalovirus Early Glycoprotein", *J. Virology* 63(8):3330-3337, Aug. 1989.
M. Ho, Cytomegalovirus Biology and Infection, Plenham Publishing Corp., New York, 275 pages (pp. 9-30, 55-61 and 79-105) (1982).
F. Rapp, *Comprehensive Virology* 16, 193-232 (1980).
T. Maniatis et al., *Molecular Cloning: A Laboratory Manual*, 521 pages (pp. 309-353 and 435-478), Cold Spring Harbor Laboratory, Cold Spring Harbor, N.Y. (1982).
D. Gretch et al., *J. Vir.*, 62, 875-881 (1988).
W. Britt et al., *J. Vir.*, 63, 403-410 (1989).
D. Gretch et al., *J. Gen. Vir.*, 69, 1205-1215 (1988).
M. Cranage et al., *EMBO J.*, 5, 3057-3063 (1986).
M. Mach et al., *J. of Gen. Vir.*, 67, 1461-1467 (1986).
K. Weston et al., *J. of Mol. Bio.*, 192:177-208 (1986).
M. Cranage et al, *J. Virol.*, 62, 1416-1422 (1988).
C. P. Chang et al., *J. Virol., 63, 281-290 (Jan. 1989)*.
M. Stinski, *J. Virol.*, 26, 686-701 (1978).
M. Wathen, *J. Virol.*, 41, 462-477 (1982).
A. Berk and P. Sharp, Cell, 12, 721-732 (1977).
R. Stenberg et al., *J. Virol.*, 49, 190-199 (1984).
C. Yanisch-Perron et al., *Gene*, 33, 103-119 (1985).

(List continued on next page.)

*Primary Examiner*—John J. Doll
*Assistant Examiner*—Robert D. Budens
*Attorney, Agent, or Firm*—Merchant, Gould, Smith, Edell, Welter & Schmidt

[57] ABSTRACT

The present invention provides an envelope glycoprotein which is encoded by an early structural gene of human cytomegalovirus, and polyclonal and monoclonal antibodies to the early envelope glycoprotein.

5 Claims, 5 Drawing Sheets

OTHER PUBLICATIONS

D. Melton et al., *Nucleic Acids Res.* 12, 7035–7056 (1984).

T. Hermiston et al., *J. Virol.*, 61, 3214–3221 (1987).

H. Towbin et al., *Proc. Nat. Acad. Sci. USA, 76, 4350–4354 (1979).*

M. Stinski, *J. Virol.*, 19, 594–609 (1976).

J. Stringer et al., *J. Virol.*, 27, 56–73 (1978).

M. Wathen et al., *J. Virol.*, 38, 446–459 (1981).

R. Stenberg et al., *J. Virol.*, 56, 665–675 (1985).

A. Maxam and W. Gilbert, Methods Enzymol., 65, 499–560 (1980).

F. Sanger et al., *Proc. Nat. Acad. Sci. USA*, 74, 5463–5467 (1983).

M. Kozak, *J. Molecular Biol.*, 196, 947–950 (1987).

T. Hopp et al., *Proc. Nat. Acad. Sci USA*, 78, 3823–3828 (1981).

G. Kohler and C. Milstein, *Nature*, 256, 495 (1975).

Britt et al., *J. of Vir.*, 62, 3309–3318 (1988).

F. R. Cockerill, III, *Mayo Clinical Proceedings*, 60:636–638 (1985).

Davis et al, *J. of Vir.*, 52, 129–135 (1984).

J. DeMarchi, *Vir.*, 124, 390–402 (1983).

Forman et al., *J. of Immunology*, 134, 3391–3395 (1985).

Furukawa et al., *Proc. Soc. Exp. Bio. Med.*, 175, 243–250 (1984).

Goldstein et al., *Infection and Immunity*, 38, 273–281 (1982).

Gretch et al., *Anal. Bio.*, 163, 270–277 (1987).

Jahn et al., *J. of Vir.*, 49, 363–370 (1984).

Jahn et al., *J. of Vir., 61, 1358–1367 (1987).*

Keil et al., *J. of Vir.*, 61, 526–533 (1987).

Kim et al., *J. of Vir.*, 20, 604–611 (1976).

Kim et al., *J. Clin. Microbiol.*, 18, 331–343 (1983).

Liu et al., *J. of Vir.*, 62, 1066–1070 (1988).

Nowak et al., *Vir.*, 134, 91–102 (1984).

Pande et al., *Proc. Nat. Acad. Sci. USA*, 81, 4965–4969 (1984).

L. Pereira et al., *Infection and Immunity*, 36, 924–942 (1982).

L. Pereira et al., *Vir.*, 139, 73–86 (1984).

Reddehase et al. *J. Virol.* 57, 408–412 (1986).

Rüger et al., *J. Virol.*, 61, 446–453 (1987).

Shuster et al., *Mayo Clin. Proc.*, 60:577–585 (1985).

Spaete et al.., *Virol.*, 167, 207–225 (1988).

R. Stenberg et al., *J. of Vir.*, 56, 676–682 (1985).

M. Stinski et al., *J. of Vir.*, 46, 1–14 (1983).

Thomsen et al., *Proc. Nat. Acad. Sci. USA*, 81, 659–663 (1984).

B. Kari and R. Gehrz, *Arch. Virol.* 98: 171–188 (1988).

```
                                                    +1
GGA TAT GTA TAA ATG AGG AGT GAA ATA GGC ACA GGG AAT CAG  +10
ATG CCG GCC TTG TGA TGC AGC CGC TGG TTC TCT CGG CGA AAA  +52
AAC TGT CGT CTT TGC TCA CTT GCA AAT ACA TCC CGC CTT AAG  +94
TGA TGA GTC TAT AAA GCA CCG TTG TCT GGG TAC GGT AAA AGT  +136
GAC TCG GAT TGT AGC ACG TCA TTT TTT TTT GTT TTT GCA TCG  +178
TTT ATC GTC ACC ACT AGT GCA ATA TTT TGA TCG TAA GGC TGA  +220
AAG AGT ATC GTT ATG ATG CTT AGA GCG TGG AGA TTG ATG GTA  +262
                Met Met Leu Arg Ala Trp Arg Leu Met Val  (10)

CTA CTT GCC GCG TAC TGT TAT TAT GTT TTT GCG AAT TGT TCA  +304
Leu Leu Ala Ala Tyr Cys Tyr Tyr Val Phe Ala Asn Cys Ser  (25)

ATC AGC ACG ACG ACT GCT CCT GTG GAA TGG AAG TCT CCC AAC  +346
Ile Ser Thr Thr Thr Ala Pro Val Glu Trp Lys Ser Pro Asn  (39)

CGT CAG ATT CCC AAG AAT ATT ACT TGC GCT AAT TAC TCA GGG  +388
Arg Gln Ile Pro Lys Asn Ile Thr Cys Ala Asn Tyr Ser Gly  (53)

ACC GTC GGC GGT AAC GTT ACT TTT CAG GGT CTC AAG AAT AAA  +430
Thr Val Gly Gly Asn Val Thr Phe Gln Gly Leu Lys Asn Lys  (67)

ACG GAA GAT TTT TTA TCC TGG CTA CTC GCG TCT GCT TAT AAG  +472
Thr Glu Asp Phe Leu Ser Trp Leu Leu Gly Ser Gly Tyr Lys  (81)

TCC ATT TGC TCG TTC TTC CCG CAA CTC CCT GGT GAT TCT AAT  +514
Ser Ile Cys Ser Phe Phe Pro Gln Leu Pro Gly Asn Ser Asn  (95)

GAG CAG CAT TAC AGA TAT GAA GTA ACC AAC CTC ACG TAC ATT  +556
Glu Gln His Tyr Arg Tyr Glu Val Thr Asn Leu Thr Tyr Asn  (109)

TGC ACC TAT GAC CGA CTG ACG TTA CTG AAT CTG ACA ACG GAA  +598
Cys Thr Tyr Asp Arg Leu Thr Leu Leu Asn Leu Thr Thr Glu  (123)

AAC AGC AGG AAT TAC TAT TTC AGA AGA GAA GAT GCG ATT TCC  +640
Asn Ser Arg Asn Tyr Tyr Phe Arg Arg Glu Asp Ala Asn Ser  (137)

ACC TTC TAT TAC TCT TGT TAC AAT CTG ACC GTG TCC TAA AGA  +682
Thr Phe Tyr Tyr Ser Cys Tyr Asn Leu Thr Val Ser Stop    (148)
```

FIG. 2A

```
TCG CAC GTG AAG TTC CAC AGA AAC CGC GCA GCT GTA GCT ATT  +724
GTG TTT ACG TTG CTT TTG AAA TGT TAA GCG TCC CTA CGG CGC  +766
TAA CAT GTT TCT AGG CTA CTC TGA CTG TGT AGA TCC CGG CCT  +808
TGC TGC GTA TCG TGT ATC TAG ATC ACG CTT AAA GCT CGT GTT  +850
GTC TTT TGT GTG GTT GAT CGG TTT GCG TCT CCA TGA TTG TGC  +892
CAC GTT CGA GTC CTG CTG TTA CGA CAT CAC CGA GGC GGA GAG  +934
TAA CAA GGC TAT ATC AAG GGA CGA AGC AGC ATT CAC CTC CAG  +976
CGT GAG CAC TCG TAC ACC ATC CCT AGC GAT CGC GCC CCT CCT +1018
CCT GAC CGA TCG ATG CTG TTG TCG CGG GAG GAA GAA CTC GTT +1060
CCG TGG AGT CGT CTC ATC ATC ACT AAG CAG TTC TAC GGA GGC +1102
CTG ATT TTC CAC ACC ACC TAG GTC ACC CGG CTT CGT CTT GCT +1144
AGG ACT TTT GAC GCT TTT CGC CAG CCT GTT TCG CGT ACC CAC +1186
AAT CCA TCT GTC GTT TCT GCA TAG ACC GTC TCC GGG ACA TCG +1228
CCC GTC CTC TGA AAT ACC GCT ATC AAC GTC TCG TCG CTA CCG +1270
TGT AGC TAG TTA GCC AGC TGT GTA TAG TTT GTT GTG TTT TGC +1312
TTT TGC ATA TTT GTT TTC AGT CAG AGA GTC TGA AAC GGG GTG +1354
GGA GGG ACT TTT GCG GGT AGT GCA CGC TAA GAT GAA CGG GTG +1396
GGC TGG GGT GTG CTT GAT AAC TCA CTG TTT GAA TAC CGA TCA +1438
CGC ACA TAT GTA GCA CTC AAC ATG TTA GCA TTT GCC CGC ACG +1480
CCC CGG GGC ATG CCG AGC TGC CTT TTT AAT AAA GTC TGG GTT +1522
TCC AGA TAC GCG CTG GTT CTG ATT TTG ATG GTT TGT GCC TCT +1564
```

CGGGGGATAG TGAGGAATTC TCAGGGGATG ATATGGGACC CAATCACTGG ATAAGACAAG
−133

GGTTTTTCCC CGTAAGATGA TCCTCGTATC ACATGAGGTC TGGATATGTA TAAATGAGGA
−73

GTGAAATAGG CACAGGGAAT CAGATGCCGG CCTTGTGATG CAGCCGCTGG TTCTCTCGGC
−13          +1                       ▲
                                     Δ1

GAAAAACTG TCGTCTTTGC TGACTTGCAA ATACATCCCG CCTTAAGTGA TGAGTCTATA
+48                                ▲
                                  Δ5

AAGCACCGTT GTCTGGGTAC GGTAAAAGTG ACTCGGATTG TAGCACGTCA TTTTTTTTTG
+108                              ▲
                                 Δ13

TTTTTGCATC GTTATCGTC ACCACGAGTG CAATATTTTG ATCGTAAGGC TGAAAGAGTA
+168                           ▲
                              Δ16

TCGTTATGAT GCTTAGAGCG TGGAGATTGA TGGTACTACT TGCCGCGTAC TGTTATTATG
+228

TTTTTGCGAA TTGTTCAATC AGCACGACGA CTGCTCCTGT GGAATGGAAG TCTCCCAACC
+288

FIG. 4

OPEN READING FRAME 1

MFLRIVQSARRLLLWNGSLPTVRFPRILLALITQGPSAVT        40
    1-1

LLFRVSRIKRKIFYPGYSGLVISPFARSSRNSLVILMSSI        80
TDMK                         1-2

FIG. 5A

OPEN READING FRAME 3

MMLRAWRLMVLLAAYCYYVFANCSISTTTAPVEWKSPNRQ        40

IPKNITCANYSGTVGGNVTFQGLKNKTEDFLSWLLGSGYK        80

SICSFFPQLPGDSNEQHYRYEVTNLTYNCTYDRLTLLNLT        120
               2-1

TENSRNYYFRREDANSTFYYSCYNLTVS
2-2

FIG. 5B

EARLY ENVELOPE GLYCOPROTEIN OF HUMAN CYTOMEGALOVIRUS (HMCV) AND MONOCLONAL ANTIBODIES TO THE GLYCOPROTEINS

STATEMENT REGARDING FEDERALLY-FUNDED RESEARCH

This invention was made with Government support under Public Health Service Grant No. HD-19937. The Government may have certain rights in the invention.

FIELD OF THE INVENTION

The present invention relates to an early structural gene of human cytomegalovirus (HCMV), and to an HCMV envelope glycoprotein and its polypeptide precursor which can be coded for by the early gene. That envelope glycoprotein has been shown to elicit an immune response in humans based on the presence of antibodies to the glycoprotein in human anti-HCMV convalescent serum. Furthermore, peptides from predicted antigenic regions of the polypeptide precursor elicit antibodies in rabbits which react with the precursor and with the glycoprotein.

BACKGROUND OF THE INVENTION

Human cytomegalovirus is the most common cause of congenital infection leading to mental retardation, deafness, and other neurological handicaps in the United States. Moreover, immunocompromised patients, such as those with cancer, acquired immunodeficiency syndrome (AIDS) and organ transplant recipients are at high risk for developing HCMV infection. M. Ho, *Cytomegalovirus Biology and Infection*, Plenum Publishing Corp., New York, 1-275 (1982); F. Rapp, *Comprehensive Virology*, 16, 193-232 (1980).

HCMV is a member of the family herpesviridae. HCMV virions consist of a linear double-stranded DNA molecule enclosed within an icosahedral nucleocapsid, surrounded by a tegument and a lipid-containing envelope containing a number of viral glycoproteins and glycoprotein complexes. Several distinct viral glycoproteins have been identified in the envelope of HCMV by the utilization of monoclonal antibody technology to immunoprecipitate the glycoproteins. See, for example, D. Gretch et al., *J. Virol.*, 62, 875-881 (1988). Some of these glycoproteins are in disulfide-linked complexes that can be separated by rate zonal centrifugation. Gretch et al. have identified three glycoprotein complexes (gc) designated as gcI, gcII, and gcIII.

The major component of the outer HCMV virion envelope is the glycoprotein complex gcI, which contains a homolog of herpes simplex virus (HSV) glycoprotein B (gB). The complex gcI consists of a 55 kilodalton (kDa) glycoprotein, designated as gp55, in a disulfide-linked complex with a heterogeneous glycoprotein designated as gp93-130. W. Britt et al., *J. Virol.*, 63, 403-410 (1989); D. Gretch et al., *J. Gen. Virol.*, 69, 1205-1215 (1988). The gene encoding gp55 has been identified, and maps between 0.344 and 0.360 map units (m.u.). This gene exhibits extensive homology with the glycoprotein B gene of herpes simplex virus (HSV) type 1. M. Cranage et al., *EMBO J.*, 5, 3057-3063 (1986); M. Mach et al., *J. Gen. Virol.*, 67, 1461-1467 (1986).

A second set of antigenically related complexes, designated gcII, appears to represent multimeric forms of one or more gene products. The isolation and characterization of the principal glycoprotein contained within this family of complexes, gp47-52, has been described in detail in co-pending U.S. patent application Ser. No. 06/933,789, filed Nov. 24, 1986, wherein it is referred to as GLP-B, and in co-pending U.S. patent application Ser. No. 07/158,389, filed Feb. 22, 1988, wherein it is referred to as gp52(II).

K. Weston et al., *J. Mol. Biol.*, 192, 177-208 (1986), have sequenced the short unique ($U_s$) region of the HCMV genome (AD169 strain), revealing at least 38 open reading frames (ORFs) that potentially code for (glyco)proteins of HCMV. One gene family, designated HXLF (HindIII X left reading frame), consists of five ORFs that lie in tandem with varying degrees of homology. The HXLF1 and HXLF2 genes code for proteins of 21 to 25 kDa and 20 kDa, respectively, which are glycosylated to glycoproteins of 47 to 52 kDa (gp47-52). D. Gretch et al., *J Virol.*, 62, 875-881 (1988).

Glycoproteins with molecular weights of 86 kDa and 145 kDa have been isolated from a third HCMV glycoprotein complex, designated as gcIII. gp86 is a homolog of HSV gH. The gene encoding gp86 has been identified, and maps between 0.45 and 0.47 m.u. M. Cranage et al., *J. Virol.*, 62, 1416-1422 (1988). The gene which encodes gp145 has not been identified, however.

Gene expression of the human cytomegalovirus can be broadly categorized in three functional phases, immediate-early (IE), early, and late. The genes relating to these phases are transcribed in sequential order beginning with the restricted transcription of IE genes. These IE genes are in a large, unique genome segment that encodes for the regulatory proteins required for the subsequent expression of early genes involved in DNA replication and late genes encoding for structural proteins and glycoproteins in mature virions. This genome segment is the $U_L$ region. In particular, this region includes three IE genes and a promotor-regulatory segment (the IE transcriptional regulatory unit) that controls the temporal expression of all the genes of the HCMV genome. Each IE gene encodes one or more mRNA transcripts which code for the regulatory proteins.

The mechanisms that regulate expression of viral early and late genes and the functions of their products are important to the replication of HCMV. The early genes are expressed but their products are unknown at present. Therefore, it is an object of the present invention to identify the early viral envelope glycoproteins of HCMV and their polypeptide precursors, and to identify and characterize the genes encoding these proteins, a further object is to determine the immunogenicity of these proteins and develop antibodies and vaccines against them.

SUMMARY OF THE INVENTION

The present invention is directed to an early structural gene of human cytomegalovirus (HCMV), a recombinant expression vector which comprises the gene, an early envelope glycoprotein of HCMV which can be coded for by the gene, a polypeptide derivative relating to the early gene, polyclonal and monoclonal antibodies to the early envelope glycoprotein and polypeptide, a vaccine and diagnostic methods which utilize the glycoprotein.

More specifically, the present invention provides a substantially pure early structural gene of HCMV. This gene maps (i.e. is found) between about 0.054 and 0.064 map units (m.u.) of the HCMV genome, and includes a major open reading frame designated herein as "ORF3." See C. P. Chang, C. L. Malone and M. F. Stinski, *J. Virology*, 63, 281-290 (January, 1989); the disclosure of which is incorporated herein by reference. The AUG initiation codon for ORF3 is located at 233 base pairs (bp) downstream from the major early transcription start site of an early mRNA transcribed from the HCMV early gene. As used herein, "structural gene" means a gene that determines amino acid sequences of polypeptides that comprise structural components of HCMV virions, in contrast to a "regulatory gene," which either acts directly (in cis) to repress or induce adjacent genetic elements, or that determines polypeptides that regulate (in trans) the expression of other HCMV genes.

The present invention also provides a recombinant expression vector which includes foreign DNA and at least a portion of the present HCMV early gene. As used herein, the term "foreign" means that the DNA is obtained from one or more sources other than the genome of the cells within which it is ultimately expressed. The present vector comprises a promoter that allows for the high level expression of foreign mRNA, which can then be translated in vitro. As used herein, the term "express" means that the present HCMV early gene can be stably incorporated into a recombinant expression vector, introduced into an appropriate procaryotic or eucaryotic cell, and transcribed to obtain the mRNA representing the open reading frame (ORF3) for said gene.

The present invention also provides a new HCMV glycoprotein which is a substantially pure, immunogenic, early envelope glycoprotein of HCMV having a molecular weight of about 48 kDa. This glycoprotein is expressed within about twenty-four (24) hours post-infection (h.p.i.) with HCMV, or in other words is an early glycoprotein. The 48 kDa glycoprotein is coded for by the foregoing HCMV early gene. An "immunogenic" glycoprotein (or an immunogenic polypeptide mentioned below) can cause an immune response in a mammal inoculated with the glycoprotein (or polypeptide). Preferably, such a glycoprotein (or polypeptide) will cause an antibody-antigen reaction in human serum taken from persons infected with HCMV.

The present invention also provides an immunogenic, nonglycosylated early polypeptide derivative which is encoded by at least part of the DNA of the foregoing HCMV early gene. Included are the polypeptide encoded for by essentially the entire early gene and polypeptide compounds resulting from (1) at least one amino acid (AA) residue addition to the chain ends of, (2) at least one AA residue substitution within, (3) at least one AA residue insertion within, or (4) at least one AA residue deletion from the polypeptide backbone of the polypeptide. Preferrably, these manipulations will produce polypeptide compounds with as few as 4 to 5 amino acid residues or as many as about twice the number in the 17 kDa polypeptide. Especially preferred are polypeptide compounds with from about one to about 50, most especially up to 30 amino acid residue manipulations relative to the 17 kDa polypeptide chain. These polypeptide derivatives display at least some immunoreactive activity or cross-activity toward polyclonal or monoclonal antibodies raised against the 17 kDa polypeptide embodiment discussed below.

A preferred embodiment of the early polypeptide derivative has a molecular weight of about 17 kDa (p17), is coded for by the entire foregoing HCMV early gene, and can be a nonglycosylated precursor of the present 48 kDa glycopeptide. This 17 kDa polypeptide is the "polypeptide back-bone" of the 48 kDa glycopeptide.

The amino acid sequence of the early polypeptide derivative is based upon the formula for the 17 kDa embodiment. Accordingly, the present invention includes a polypeptide of the formula for the 17 kDa embodiment:

Met—Met—Leu—Arg—Ala—Trp—Arg—Leu—Met—Val—Leu—Leu—
Ala—Ala—Tyr—Cys—Tyr—Tyr—Val—Phe—Ala—Asn—Cys—Ser—
Ile—Ser—Thr—Thr—Thr—Ala—Pro—Val—Glu—Trp—Lys—Ser—
Pro—Asn—Arg—Gln—Ile—Pro—Lys—Asn—Ile—Thr—Cys—Ala—
Asn—Tyr—Ser—Gly—Thr—Val—Gly—Gly—Asn—Val—Thr—Phe—
Gln—Gly—Leu—Lys—Asn—Lys—Thr—Glu—Asp—Phe—Leu—Ser—
Trp—Leu—Leu—Gly—Ser—Gly—Tyr—Lys—Ser—Ile—Cys—Ser—
Phe—Phe—Pro—Gln—Leu—Pro—Gly—Asp—Ser—Asn—Glu—Gln—
His—Tyr—Arg—Tyr—Glu—Val—Thr—Asn—Leu—Thr—Tyr—Asn—
Cys—Thr—Tyr—Asp—Arg—Leu—Thr—Leu—Leu—Asn—Leu—Thr—
Thr—Glu—Asn—Ser—Arg—Asn—Tyr—Tyr—Phe—Arg—Arg—Glu—
Asp—Ala—Asn—Ser—Thr—Phe—Tyr—Tyr—Ser—Cys—Tyr—Asn—
Leu—Thr—Val—Ser.

Also included are the polypeptide compounds that have at least one amino acid residue addition to, deletion from, insertion within or substitution within the foregoing sequence and that do not have substantially altered the immunological activity compared with the 17 kDa polypeptide embodiment. In other words, these polypeptide compounds preferably have substantially the same structural formula as that depicted but with amino acid residue variations which, while altering the structure, do not significantly affect the B or T lymphocyte recognition sites of the 17 kDa polypeptide.

The present invention also includes the glycosylated forms of the foregoing polypeptide derivatives.

The present invention further provides a labelled glycopeptide including the 48 kDa glycopeptide and a covalently bound detectable label.

A method of detecting HCMV antibodies in a physiological fluid is also provided which utilizes the labelled glycopeptide. The method provides that the labelled glycopeptides are immunoprecipitated by the HCMV antibodies in the physiological fluid, for example, HCMV-positive human sera.

Advantageously, the recombinant expression vector disclosed herein can be employed to produce immunogenic polypeptides which formally correspond to p17 or gp48. For example, a plasmid containing a portion of the present HCMV early gene, for example pSPd116, can be linearized, mRNA synthesized in vitro, and then translated under conditions whereby the corresponding polypeptides are either glycosylated or nonglycosylated. The translation products can be either analyzed by SDS-PAGE and extracted therefrom, or solubilized for immunoprecipitation as described in the examples below.

Another advantage of the present invention is that the present compositions can be combined with a pharmaceutically-acceptable vehicle to form a vaccine against HCMV. The vaccine can be parenterally administered to a mammal, in order to raise the titer of anti-HCMV antibodies in the blood of a mammal.

Additionally, the present compositions can be useful in the production of monoclonal antibodies, which in turn can be used either directly or indirectly to diagnose HCMV, or to treat HCMV infections.

The present immunogenic compositions can also be used as diagnostic reagents, for example, to detect anti-gp48 antibodies in physiological fluids, e.g. by RIA or ELISA procedures.

The compositions can also be used to produce clonal populations of antigen-specific T-helper and T-cytotoxic lymphocytes, which in turn can be used for HCMV therapy. The production of HCMV-specific lymphocyte clonal populations and methods for their therapeutic use are described in detail in co-pending U.S. patent application Ser. No. 24,571, filed Mar. 11, 1987, the disclosure of which is incorporated by reference herein.

BRIEF DESCRIPTION OF THE DRAWINGS

FIG. 1A depicts the gene in a 5' to 3' orientation, and shows the approximate location of three potential protein coding regions or open reading frames (indicated by open blocks) located within the 0.054–0.064 m.u. region. The translation initiation codons and stop codons are depicted as open circles. FIG. 1B represents three RNA transcripts of the present gene as arrowed lines above the restriction map shown in FIG. 1C. The thickness of each arrowed line represents the approximate abundance of each RNA in HCMV-infected cells. The promoter consensus sequences and the polyadenylaton signal are indicated.

FIGS. 2A and 2B are a schematic depiction of the DNA sequence and the predicted amino acid sequence of ORF3 of the present HCMV early gene. The nucleotide sequence (top line) and the amino acid sequence of the open reading frame ORF3 (bottom line) are numbered. The transcription start site of the major early RNA is designated by a +1. The 18 amino acid sequence of a peptide designated as peptide 2-1 which was used to generate antiserum directed against ORF3 is boxed. Potential N-glycosylation sites (Asn-X-Ser/Thr) and the polyadenylation signal are underlined. The nucleotide at position +1122 was not determined.

DETAILED DESCRIPTION OF THE INVENTION

A. The HCMV Early Gene

Figure 2B:
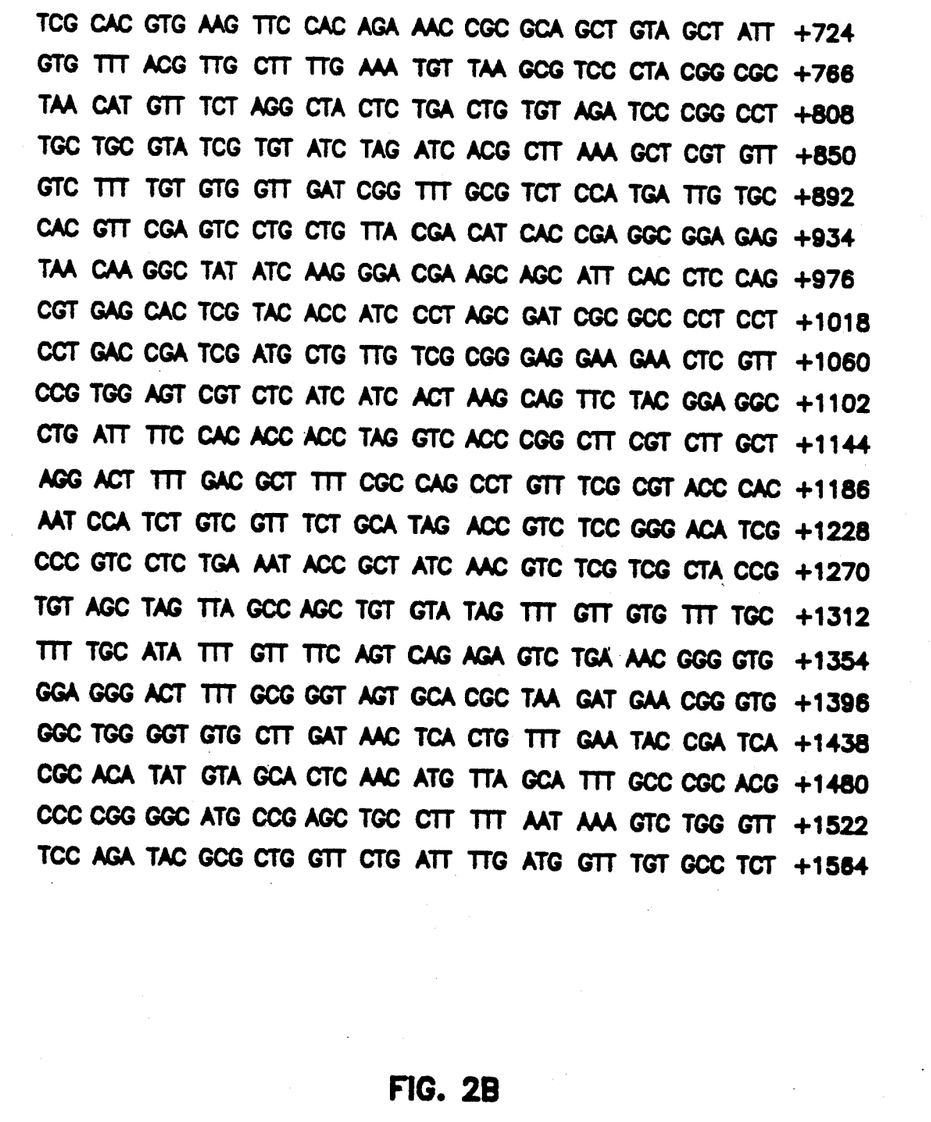

The present invention provides a substantially pure early structural gene of human cytomegalovirus (HCMV). This gene maps between about 0.054 and 0.064 map units (m.u.), and comprises a major open reading frame designated herein as "ORF3." As shown in FIG. 2, the AUG initiation codon for ORF3 is located at 233 base pairs (bp) downstream from the major early transcription start site of an early mRNA transcribed from the HCMV early gene. This mRNA is a 1.5 kb (1500 nucleotide) major early mRNA which contains a 232-base 5' untranslated sequence and an 860-base 3' untranslated sequence.

In a preferred embodiment of the present HCMV early gene, the expression of the gene is under the control of three temporally regulated promoters. Analysis of the promoter region of the HCMV early gene resulted in the isolation of three unspliced, overlapping RNAs transcribed from different initiation sites and terminating at the same 3' end of the gene. Three individual promoters for these RNA transcripts were also isolated which were regulated differently during the course of infection. Two early RNA transcripts were identified at 24 h.p.i., and an additional late RNA transcript was also identified.

B. Recombinant Expression Vector

Figure 4:
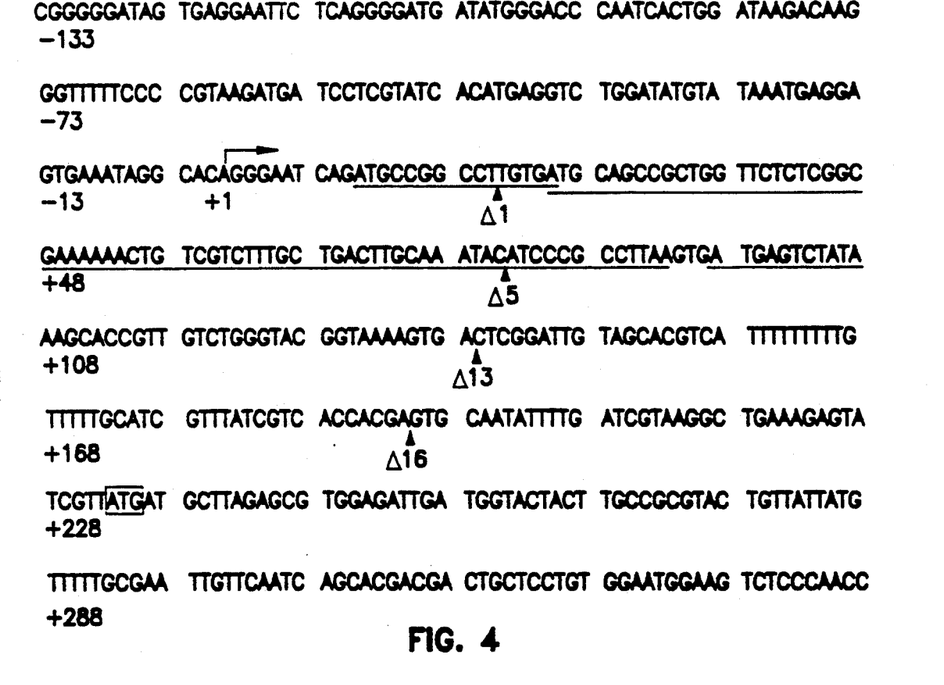
FIG. 4 is a schematic depiction of the nucleotide sequence of the 5' noncoding region (NCR) of the HCMV early gene and its deletion plasmid clones. The major early transcription start site is numbered +1 and marked with an arrow. The first ATG of ORF3 is boxed, and the three short upstream ORFs are underlined. The 3' boundaries of the deletion plasmid clones are indicated by arrowheads.

The present invention also provides a recombinant expression vector comprising foreign DNA and at least a portion of the present HCMV early gene. The present vector comprises an inducible promoter which, in the presence of SP6 RNA polymerase, allows for the high level expression of the foreign gene to obtain mRNA, which can then be translated in vitro. Preferably, the present recombinant expression vector comprises a plasmid designated herein as "pSPd116." This plasmid begins at 195 nt downstream from the major early transcription start site of the present HCMV early gene, as indicated in FIG. 4 herein. As further described in the examples below, pSPd116 was generated by progressive modification of the 5' leader region of the HCMV early gene.

This 5' leader region comprises the first short open reading frame located upstream from ORF3 (the first underlined sequence in FIG. 4), and additional nucleotide sequence up to position +81. The 5' region, thus defined, contains a repressor which prevents translation of ORF3.

C. The Early Envelope Glycopeptide

The present invention also provides new HCMV polypeptides and glycoproteins. A preferred glycoprotein of the present invention is a substantially pure, immunogenic, early envelope glycopeptide of HCMV having a molecular weight of about 48 kDa. As used herein with respect to the present glycopeptide, "early" means that the glycopeptide is expressed within about twenty-four (24) hours post-infection (h.p.i.) with HCMV. The 48 kDa glycopeptide is preferably coded for by the HCMV early gene which comprises ORF3.

The 48 kDa glycopeptide can comprise both N- and O-linked glycosylation sites.

According to the present invention, the 48 kDa glycopeptide may further comprise a detectable label such as a radioactive isotope, and be utilized in a method of detecting HCMV antibodies in a physiological fluid. The present method provides that the labelled glycopeptides are immunoprecipitated by the HCMV antibodies in the physiological fluid, for example, HCMV-positive human sera.

D. The Polypeptide Precursor

The present invention also provides an immunogenic, nonglycosylated early polypeptide derivative of HCMV which is encoded for by at least part of the DNA of the foregoing HCMV early gene. Included are the 17 kDa polypeptide embodiment and its peptide residue additions, substitutions, insertions and deletions that display at least some immunoreactive activity or cross-activity toward polyclonal or monoclonal antibodies raised against the 17 kDa polypeptide embodiment. Preferably, the polypeptide compounds formed by the foregoing peptide residue manipulations have at least the same amino acid sequences as the hydrophilic and/or hydrophobic antigenic domains or the epitopal sites of the 17 kDa polypeptide embodiment. These domains or sites relate to T cell or B cell immunoreactivity. The 17 kDa polypeptide (p17) is coded for by the entire HCMV early gene which comprises ORF3. The 17 kDa polypeptide can be a precursor of the present 48 kDa glycopeptide, and is also referred to herein as the "polypeptide backbone" of the 48 kDa glycopeptide.

The 148 amino acid sequence of the 17 kDa polypeptide has the formula:

Met—Met—Leu—Arg—Ala—Trp—Arg—Leu—Met—Val—Leu—Leu—
Ala—Ala—Tyr—Cys—Tyr—Tyr—Val—Phe—Ala—Asn—Cys—Ser—
Ile—Ser—Thr—Thr—Thr—Ala—Pro—Val—Glu—Trp—Lys—Ser—
Pro—Asn—Arg—Gln—Ile—Pro—Lys—Asn—Ile—Thr—Cys—Ala—
Asn—Tyr—Ser—Gly—Thr—Val—Gly—Gly—Asn—Val—Thr—Phe—
Gln—Gly—Leu—Lys—Asn—Lys—Thr—Glu—Asp—Phe—Leu—Ser—
Trp—Leu—Leu—Gly—Ser—Gly—Tyr—Lys—Ser—Ile—Cys—Ser—
Phe—Phe—Pro—Gln—Leu—Pro—Gly—Asp—Ser—Asn—Glu—Gln—
His—Tyr—Arg—Tyr—Glu—Val—Thr—Asn—Leu—Thr—Tyr—Asn—
Cys—Thr—Tyr—Asp—Arg—Leu—Thr—Leu—Leu—Asn—Leu—Thr—
Thr—Glu—Asn—Ser—Arg—Asn—Tyr—Tyr—Phe—Arg—Arg—Glu—
Asp—Ala—Asn—Ser—Thr—Phe—Tyr—Tyr—Ser—Cys—Tyr—Asn—
Leu—Thr—Val—Ser.

The polypeptide derivatives incorporate at least substantial portions of this formula, the remaining portions being amino acid residue substitutions, deletions, additions or insertions such that the derivative does not have substantially altered biochemical or immunological activity compared with the 17 kDa polypeptide.

The invention will be further described by reference to the following detailed examples, wherein the methodologies were as described below. The disclosures of the cited references are incorporated by reference herein.

Virus and Cells. The culturing of human foreskin fibroblast (HFF) cells, the propagation of HCMV (Towne strain), and the use of phosphonoacetic acid (PAA) to inhibit viral DNA replication have been described by M. Stinski, *J. Virol.*, 26, 686–701 (1978); and M. Wathen, *J. Virol.*, 41, 462–477 (1982). All experiments were conducted at 5–10 plaque-forming units (p.f.u.)/ml.

RNA Structural Analysis. RNA structure was determined by the nuclease mapping technique described by A. Berk and P. Sharp, *Cell*, 12, 721–732 (1977), with mung bean nuclease (Pharmacia Inc., Pistcataway, N.J.) and ExoVII (Bethesda Research Laboratories, Gaithersburg, Md.) as described by R. Stenberg et al., *J. Virol.*, 49, 190–199 (1984).

Hybridization temperatures were determined empirically for each DNA probe. Each probe was labeled according to the standard protocol of T. Maniatis et al., *Molecular Cloning: A Laboratory Manual*, Cold Spring Harbor Laboratory, Cold Spring Harbor, N.Y. (1982). The probes were labeled either at the 5' end by using T4 polynucleotide kinase (Pharmacia Inc., Pistcataway, N.J.) or at the 3' end by using the Klenow fragment of *E. coli* DNA polymerase I (Boehringer Mannheim Biochemicals, Indianapolis, Ind.). In some experiments, plasmid DNAs were uniformly labeled in vivo by growing *E. coli* in dephosphorylated LB broth in the presence of $^{32}P_i$ Amersham Corp., Arlington Heights, Ill.) as described by R. Stenberg et al., *J. Virol.*, 49, 190–199 (1984). The uniformly labeled probes were digested with appropriate restriction enzymes and recovered after gel electrophoresis.

Probes were hybridized to the same quantity of RNA (20 μg) isolated from mock-infected or infected cells at various times after infection. Nuclease-resistant hybrids were analyzed in neutral or alkaline 1.0 to 1.4% agarose gels or in 8% polyacrylamide-7M urea gels, using pSV325-HindIII and pBR322-EcoRI-HinfI fragments as standard size markers. Relative amounts of RNA were quantified by autoradiogram scanning, using a DU-8 spectrophotometer (Beckman Instruments, Inc., Fullerton, Calif.).

Figure 1A:
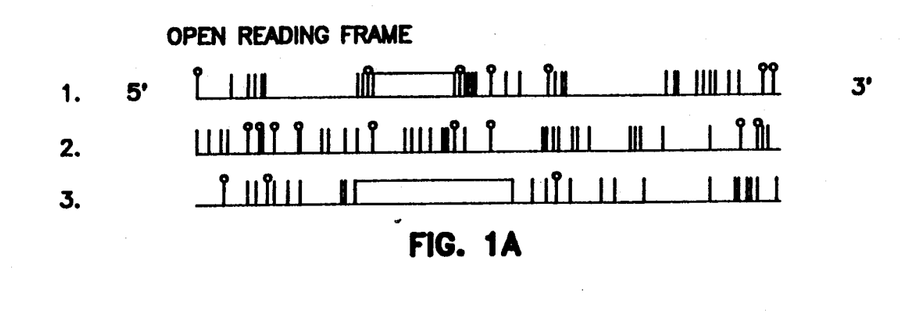
FIGS. 1A–1C are schematic depictions of the organization of the HCMV early gene localized between 0.054 and 0.064 map units.
Figure 1B:
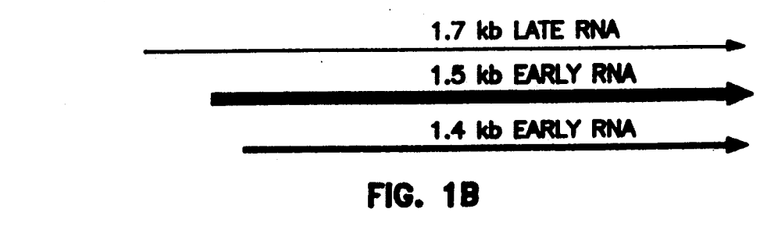
Figure 1C:
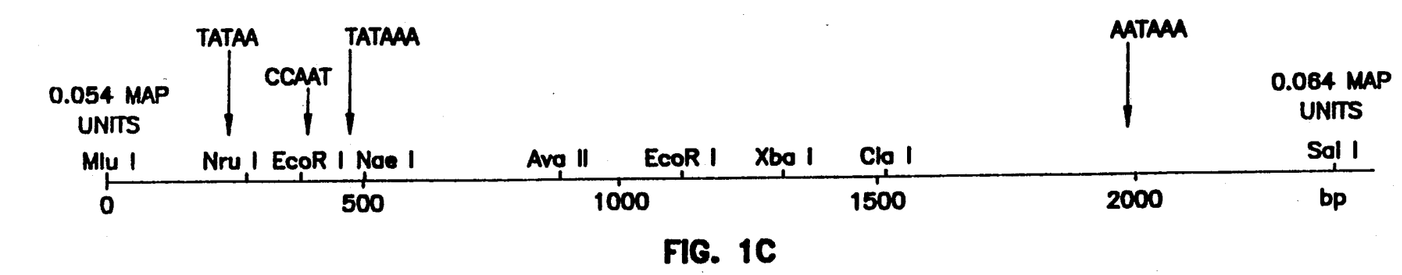

Plasmid Construction. For construction a series of deletion plasmids in the 5' noncoding region (NCR) of the present HCMV early gene, pUCMS, a pUC19-derived plasmid containing the entire HCMV early gene from the MluI site (0.054 m.u.) to the SalI site (0.064 m.u.) as depicted in Panel C of FIG. 1, was utilized as starting material. pUC19 is a general cloning vector of the pUC series. See Vieira and Messing, *Gene*, 33, 103 (1985). pUCMS was linearized at the unique NruI site and digested with exonuclease III (Bethesda Research Laboratories, Gaithersburg, Md.) followed by mung bean nuclease (Pharmacia Inc., Pistcataway, N.J.). HindIII linkers were added to the blunt ends. The shortened inserts were released from the pUC19 vector by digestion with HindIII and PstI, and then inserted into the corresponding sites of plasmid pSP64 according to D. Melton et al., *Nucleic Acids Res.*, 12, 7035–7056 (1984).

The deletion endpoints of four plasmid clones designated pSPd11, pSPd15, pSPd113, and pSPd116, respectively, were determined by sequencing the plasmids with SP6 promoter primer according to the protocol supplied by the manufacturer (Boehringer Mannheim Biochemicals, Indianapolis, Ind.).

The trpE fusion protein vector pATH1 was a gift from Lung-Ji Chang, University of California at San Francisco. The vector pATH1, which contains a truncated trpE gene coding for a 37 kDa protein, was used to construct an ORF3-trpE fusion gene by inserting a 640 base pair (bp) DNA fragment into BamHI-digested pATH1. The resulting plasmid was designated pATH-1ORF3.

In Vitro Transcription. The 5' NCR deletion plasmids were linearized with BamHI or EcoRI (pSPd116 only), extracted with phenol-chloroform, and precipitated with ethanol. The conditions utilized for in vitro transcription using SP6 RNA polymerase were those according to D. Melton et al., Nucleic Acids Res., 12, 7035–7056 (1984).

In Vitro Translation. Standard translation, using [14$^C$] leucine (342 mCi/mmole, at 50 $\mu$Ci/ml; Amersham, Arlington Heights, Ill.) as the labeled amino acid in wheat germ extracts, was preformed as described by the supplier (Promega Biotec, Madison, Wis.). Approximately one-fifth of the resultant sample was analyzed directly by SDS-polyacrylamide gel electrophoresis (SDS-PAGE).

Figure 5A:
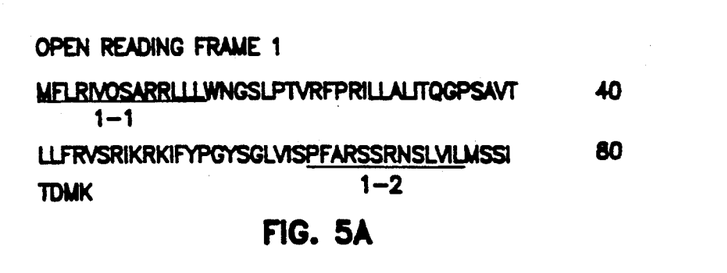
FIGS. 5A and 5B are schematic depictions of the predicted amino acid sequences of open reading frames ORF1 and ORF3 using a single letter code. The sequences of the synthetic peptides 1-1, 1-2, 2-1, and 2-2 used for generation of antibodies are underlined. The amino acid numbers are indicated at the right margin.
Figure 5B:
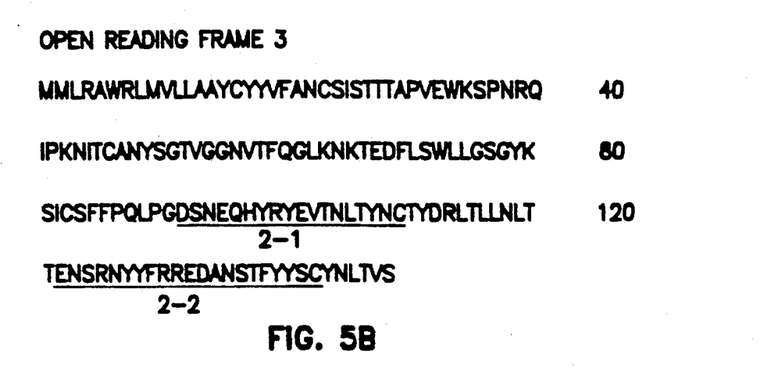

Antisera. Peptides used for generating antibodies were synthesized at the Peptide Oligonucleotide Synthesis Facility at the Scripps Clinic, La Jolla, Calif., and are shown in FIG. 5. Antipeptide sera were prepared as described by T. Hermiston et al., J. Virol., 61, 3214–3221 (1987). To reduce nonspecific reactivity, the antisera were passed through a Sepharose 4B (Pharmacia Inc., Pistcataway, N.J.) column conjugated with HFF cellular proteins.

Immunoprecipitation. For immunoprecipitation of in vitro translation products, 540 $\mu$l of RIPA buffer (phosphate buffered saline [PBS], pH 7.4 containing 0.5% sodium deoxycholate, 1% Nonidet-40 [NP-40], 0.1% SDS, 1 mg/ml ovalbumin, 0.02% sodium azide [NaN$_3$], and 1 mM phenylmethylsufonyl fluoride) and 10 $\mu$l of antipeptide serum 2-1 were added to the reaction mixture, and incubated at 4° C. overnight.

For immunoprecipitation of metabolically labeled antigens, HCMV-infected or mock-infected cells were pulse-labeled from 48 to 72 h.p.i. with 40 $\mu$Ci/ml [$^3$H] glucosamine (33 Ci/mmole, Amersham, Arlington Heights, Ill.), and then solubilized in RIPA buffer. The clarified lysates were preabsorbed with normal rabbit serum and protein A-Sepharose CL-4B (Pharmacia Inc., Piscataway, N.J.). An appropriate amount of antiserum was then added to the lysate (5-10 × 10$^6$ cpm) and incubated at 4° C. overnight. Immune complexes were recovered by incubation with 50 $\mu$l of 50% suspension of protein A-Sepharose at room temperature for 1 hour. The beads were washed three times with PBS containing 0.1% NP-40, and once with sterile water. Antigens were eluted and analyzed by SDS-PAGE and autoradiography utilizing the procedures described by M. Stinski, J. Virol., 26, 686–701 (1978).

Immunoblotting. Mock or HCMV-infected cells were washed with PBS and solubilized in SDS-PAGE sample buffer. The proteins were separated in 10% or 15% SDS-polyacrylamide gels and electrophoretically transferred to nitrocellulose sheets according to the method of H. Towbin et al., Proc. Natl. Acad. Sci. USA, 76, 4350–4354 (1979). After transfer, the blots were immersed in milk buffer (Tris buffered saline [TBS] containing 10 mM Tris-HCl, pH 7.5, 0.9% NaCl, 5% nonfat dry milk, 0.01% (v/v) antifoam A emulsion [Sigma Chemical Co., St. Louis, Mo.] and 0.01% NaN$_3$) at 4° C. overnight or at room temperature (25° C.) for 2 hours. The blots were incubated with rabbit antipeptide 2-1 serum (1:100 dilution) for 2 hours and then incubated with $^{125}$I-protein A (10$^6$ cpm/ml, Amersham, Arlington Heights, Ill.) for 1 hour in milk buffer. All incubations were performed at room temperature (25° C.) and terminated by washing the blots four times in milk buffer with 15 min per wash.

Purification of Virions and Dense Bodies. Virions and dense bodies of HCMV were purified from the extracellular fluid of infected human fibroblast cells as described by M. Stinski, J. Virol., 19, 594–609 (1976).

EXAMPLE I

Mapping the HCMV Early Gene

In the following example, cytoplasmic or polysome-associated RNA was prepared according to the methods disclosed by J. Stringer et al., J. Virol., 27, 56–73 (1978); M. Wathen et al., J. Virol., 41, 462–477 (1982). Whole-cell RNA was purified by the guanidine-cesium chloride method as described by M. Wathen et al., J. Virol., 38, 446–459 (1981).

The promoter-regulator region of an early gene in the long unique sequence adjacent to the large terminal repeat (TR$_L$) of the HCMV genome was characterized. To map the transcription units originating from this TR$_L$-flanking region, polysome-associated RNA was harvested at 24 hours postinfection (h.p.i.) from cells treated with phosphonoacetic acid (PAA) to inhibit viral DNA synthesis and analyzed by Northern blot hybridization.

Figure 3:
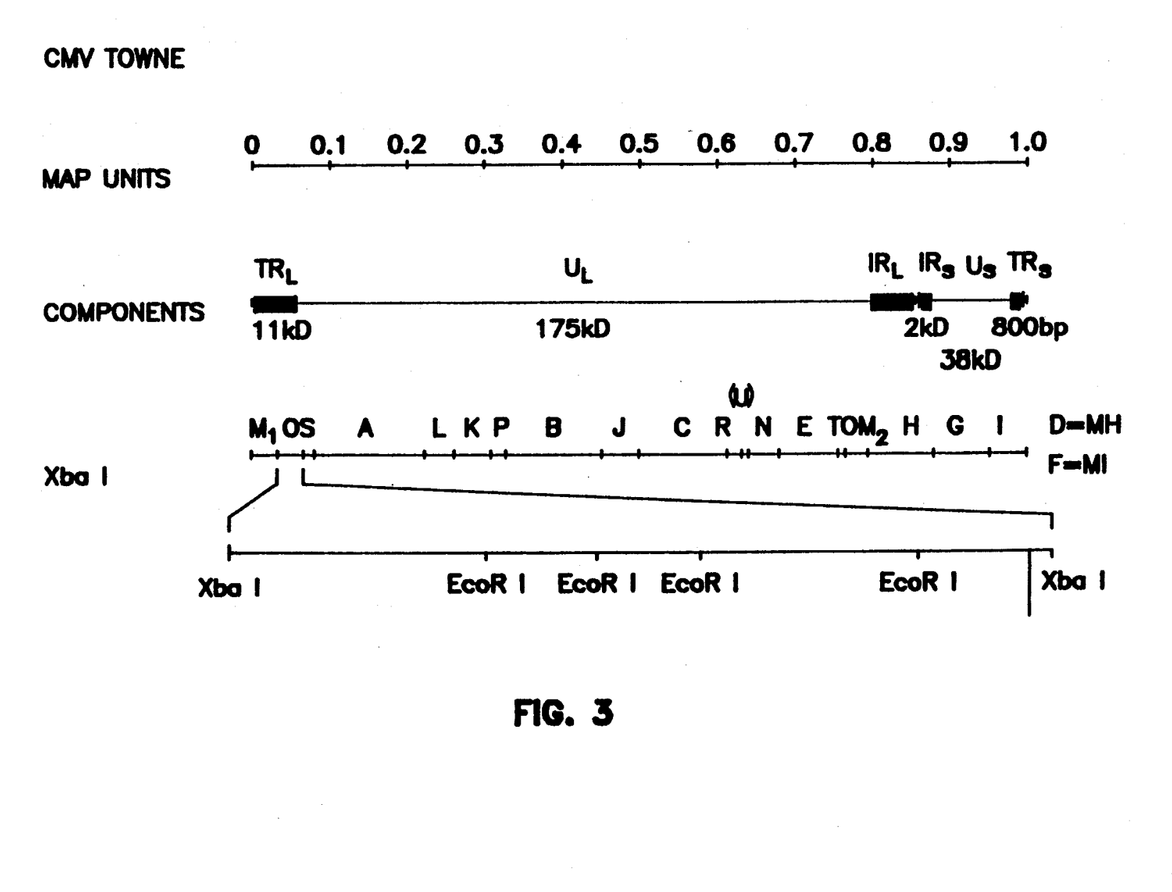
FIG. 3 is a schematic depiction of a physical map of HCMV (Towne strain) DNA. The XbaI O fragment contains a small amount of the large terminal repeat (TR$_L$) and the adjacent long unique (U$_L$) sequences.

Specific RNA transcripts were detected by using DNA probes. The XbaI-O DNA probe detected a major transcript of approximately 1.7 kilobases (kb) and two less abundant RNAs of 3.4 and 2.7 kb. To localize the region encoding the major transcript, other strips of the same RNA blot were hybridized with five consecutive XbaI-O DNA subfragments as shown in FIG. 3. The major 1.7 kb RNA hybridized with a DNA probe located to the right of the large terminal repeat (TR$_L$). Therefore, the 1.7 kb transcript originated from the long unique component of the HCMV genome. The 2.7 kb and 3.4 kb transcripts were mapped to the left half of the XbaI-O fragment, and were not characterized further.

To determine the precise location of the 1.7 kB transcript, single-stranded nuclease protection experiments were performed. Plasmid pHindIII-O was uniformly labelled in vivo with $^{32}$P$_i$ and various restriction fragments were isolated. These fragments were hybridized to polysome-associated RNA harvested from infected cells not treated with PAA at a time when both early and late RNA would be present. The resulting hybrids were digested with either mung bean nuclease (Pharmacia, Inc., Pistcataway, N.J.), or ExoVII (Bethesda Research Laboratories, Gaithersburg, Md.), according to the method of R. Stengberg et al., J. Virol., 56, 665–675 (1985). The protected DNA fragments were then analyzed by denaturing or neutral gel electrophoresis.

A major band of approximately 1,500 nucleotides (nt) and two minor bands of approximately 1,850 and 1,350 nt were detected by a 4.1 kb PstI-to-SalI DNA fragment (designated as probe 1) after treatment with mung bean nuclease or ExoVII and electrophoresis in a denaturing gel. Probe 1 as well as probe 2, a 2.3 kb MluI-to-SalI DNA fragment, detected three RNAs of 1,850, 1,500 and 1,350 nt after treatment with mung bean nuclease and electrophoresis in a neutral gel. The size of the major protected RNA (1500 nt) was consistent with the size of the 1.7 kb major transcript determined by Northern blot hybridization when approximately 200 nt of poly(A) tail was taken into account.

Probe 3, a 1.35-kb AvaII-to-AvaII DNA fragment, detected a single 1,200 nt band, and probe 4, a 3.0-kb XbaI-to-HindIII DNA fragment, detected a single 700 nt band. These results suggested that the RNAs from the present HCMV early gene have a common end on one side and heterogeneity on the other, and that the RNAs were probably not spliced, since protected fragments of a similar size were detected by mung bean nuclease or Exo VII treatment as well as by subsequent electrophoresis in alkaline or neutral gels.

This interpretation was further supported by protection experiments conducted with additional probes 5 through 8. After mung bean nuclease digestion and fractionation on a 6% polyacrylamide gel, no protection was observed with probe 6 (a 0.23 kb MluI-to-AvaII DNA fragment) and probe 7 (a 0.20 kb AvaII-to-AvaII DNA fragment), but a 400 nt band was detected by probe 8 (a 0.48 kb AvaII-to-AvaII DNA fragment), in agreement with the location of the 1.7 kb RNA. Although probe 5 detected a band of 530 nt, this band was too large to be an upstream leader exon. This band was more likely the end of a transcript expressed from the upstream flanking regions.

Based upon these results, the location of the 1.7 kb transcription unit of the HCMV early gene was assigned to 0.054 to 0.064 m.u.

Further characterization of the promoter region of the 1.7 kb transcription unit was performed at various times after infection. Three unspliced, overlapping RNAs were transcribed from different initiation sites and terminated at the same 3' end. Additionally, individual promoters were isolated for all three overlapping RNA transcripts. In the viral genome, the three promoters were regulated differently during the course of infection. Nuclease mapping and primer extension analyses detected two early RNA transcripts at 24 h.p.i., as well as an additional late RNA transcript.

In order to corroborate the existence of the three promoters, the promoters were activated in trans by viral immediate-early (IE) regulatory proteins after either infection or cotransfection with either the IE2 gene or the IE1 plus IE2 genes of HCMV, described previously by W. Hermiston et al., *J. Virol.*, 61, 3214–3221 (1987), the disclosure of which is incorporated herein by reference. Additional characterization of the promoter region of the HCMV early gene was performed as described by C. Chang et al., *J. Virol.*, 63, 281–290 (Jan. 1989), the disclosure of which is incorporated by reference herein.

EXAMPLE II

Open Reading Frame Analysis

Open reading frame analysis of the DNA sequence of the HCMV early gene between 0.054 and 0.064 m.u. revealed the presence of two overlapping open reading frames (ORFs). The first, designated ORF1, was predicted to code for 84 amino acids. The other, designated ORF3, was predicted to code for 148 amino acids. These two ORFs are depicted as open boxes in lines 1 and 3 of FIG. 1, panel A. The AUG initiation codon of ORF3 was located 233 base pairs (bp) downstream from the major early transcription start site (shown by a +1 in panel A of FIG. 4) of the present HCMV early gene. The initiation codon (ATG) of ORF1 was located 285 bp downstream from the major transcription start site.

EXAMPLE III

Nucleotide Sequence and Deduced Polypeptide

The DNA nucleotide sequence of the HCMV early gene, i.e. the 2.3 kb MluI-SalI segment shown in panel C of FIG. 1, was determined according to the methods of A. Maxam and W. Gilbert, *Methods Enzymol.*, 65, 499–560 (1980), or F. Sanger et al., *Proc. Natl. Acad. Sci. USA*, 74, 5463–5467 (1983). FIG. 2 shows the sequence from the major early transcription start site (designated by a +1) to the downstream polyadenylation signal (AAT AAA). The AUG of ORF3, located at position 233, is of moderate strength according to the rules of M. Kozak, *J. Mol. Biol.*, 196, 947–950 (1987). The AUGs of three upstream short ORFs are at position 12, 26 and 98 from the major early transcription start site, and they lie in an unfavorable context when compared to the AUG of ORF3.

The amino acid sequence of ORF3 was analyzed to generate a hydrophobicity profile by the method of T. Hopp et al., *Proc. Natl. Acad. Sci. USA*, 78, 3823–3828 (1981). Hydrophobicity profiles can be used to identify potential functional domains, for example, hydrophobic regions that can be signal sequences or transmembrane regions, or hydrophilic regions that can be accessible regions for B lymphocyte recognition (e.g. epitopal binding regions), from which synthetic peptides can be generated to induce monospecific antibodies. These are the portions of the polypeptide derivatives and the 17 kDa polypeptide embodiment that are structurally similar or the same. By tracking these portions to the early gene, those corresponding DNA sequences can be identified. The polypeptide derivatives that are amino acid residue substitutions, deletions, additions and insertions of the 17 kDa polypeptide embodiment can then be prepared by making the appropriate base codon alteration to the noncorresponding regions of the early gene and performing the recombination and expression procedures with that altered early gene and the techniques therein described for the 17 kDa polypeptide embodiment.

For the 17 kDa polypeptide embodiment, a hydrophobic signal sequence at the amino terminus and a hydrophobic carboxy terminus resembling a membrane anchorage domain were identified. Predictive amino acid analysis of the primary DNA sequence indicated that ORF3 codes for a 148-residue polypeptide which has a molecular weight of 17,132 daltons.

The 1.5 kb major early mRNA transcribed from the 2.3 kb MluI-SalI segment would contain a 232-base 5' untranslated sequence and 860-base 3' untranslated sequence. As shown in FIG. 2, the polyadenylation signal (AATAAA) is located at nucleotides 1507 through 1513. Downstream of this signal is a consensus GT cluster.

In addition, since the nucleotide sequence shown in FIG. 2 contained several Asn-X-Ser/Thr sites, it was deduced that the protein encoded for by ORF3 would have 10 potential N-linked glycosylation sites. These properties suggest that the viral gene product could be a membrane bound glycoprotein.

EXAMPLE IV

In Vitro Translation Products

Translation of hybrid-selected mRNAs in cell-free extracts was performed in order to assign a viral protein(s) to the ORFs identified in Example II, as well as to compare the assigned protein(s) with the polypeptide deduced in Example III. In vitro transcription-translation of the present HCMV early gene was also performed. However, both of these experiments failed to detect a protein, suggesting that translation was suppressed by an unknown mechanism.

Since translational regulation via the 5' untranslated region has been reported in prokaryotic and eucaryotic systems, we modified the 5' leader sequence of the HCMV early gene by progressive deletion analysis. FIG. 4 shows the nucleotide sequence of the 5' leader region of the gene which contains three tandem ORFs (underlined) upstream of the initiation codon (boxed) of the ORF3. Deletion plasmids containing a portion of the 5' leader were generated by exonuclease III digestion from the parental vector pUCMS as described in the methodologies above. The 3' boundaries of the deletion clones are indicated in FIG. 4 by arrowheads.

The effect of each deletion on translational efficiency was determined by a combination of in vitro transcription and translation. Translation products were analyzed by SDS-PAGE and autoradiography. The deletion plasmid clones pSPd11, pSPd15, PSPd113, and pSPd116 were prepared as described above. A deletion to +20 nt (pSPd11), which removed the first short ORF, did not release the block. A deletion to +81 nt (pSPd15) resulted in the appearance of a protein of approximately 17 kDa. A further deletion to +138 (pSPD113), removing all three upstream ORFs, slightly increased the translation of the 17 kDa protein. Removal of additional nucleotides from +138 to +194 (pSPd116) greatly enhanced translation of the 17 kDa protein.

The protein translated from pSPd116 (beginning at +195 nt from the major early transcription start site) was initiated from the AUG of ORF3. The evidence for this was provided by in vitro transcription and translation of EcoRI-linearized pSPd116. Since EcoRI cleaved outside of ORF1, but within the carboxy terminus of ORF3, a truncated protein was predicted. Indeed, a protein of about 15 kDA was detected.

To determine whether the HCMV early gene coded for a viral protein, antibodies directed against four synthetic peptides corresponding to different regions of ORF1 and ORF3 were prepared as described in the methodologies above. The synthetic peptides designated 1-1 and 1-2 corresponding to regions of ORF1 are underlined in the amino acid sequence shown in FIG. 5, panel A. Synthetic peptides 2-1 and 2-2 corresponding to regions of ORF3 are likewise underlined in panel B of FIG. 5. The four peptides were synthesized at the Peptide Oligonucleotide Synthesis Facility at the Scripps Clinic, La Jolla, Calif.; the antiserum against the four peptides was prepared as described by T. Hermiston et al., *J. Virol.*, 61, 3214-3221 (1987).

Generally, the antibody methods described or referred to by Hermiston can be used to prepare polyclonal and/or monoclonal antibodies to the glycoproteins or polypeptide derivatives of this invention. In particular, the hybridoma method with murine myeloma cells is advantageous for preparation of the monoclonal antibodies. See the work of G. Kohler and C. Milstein, *Nature*, 256, 495 (1975), the disclosure of which is incorporated herein by reference. Monoclonal antibodies which are capable of binding to the 48,000 dalton glycoprotein may be produced by a hydridoma formed from the fusion of murine myeloma cells and spleen cells from a mouse inoculated with the glycoprotein.

The deletion clone pSPd116 was linearized at the BamHI site as described above, and used as a template for in vitro transcription. Translation was carried out either in the presence of absence of in vitro-synthesized RNA. The translation products were subsequently immunoprecipitated with rabbit antiserum against peptide 2-1, or with a human anti-HCMV convalescent serum.

Both antisera reacted with a protein of about 17 kDa. In addition, the antiserum against peptide 2-1 recognized a smaller protein which may represent a premature termination of translation or a degraded translation product. These results demonstrate that the present HCMV early gene can direct the synthesis of a protein coded for by ORF3, and that antiserum prepared against a synthetic peptide of ORF3 (peptide 2-1) or human anti-HCMV convalescent serum contained antibodies to HCMV antigen.

EXAMPLE V

Identification of a Viral Protein in Infected Cells

Antiserum against synthetic peptide 2-1 of ORF3 was also tested for its ability to recognize a specific viral antigen in HCMV-infected cells. Cell lysates obtained from HCMV-infected or mock-infected cells at various times after infection were analyzed by Western blot analysis using the antiserum to peptide 2-1 as described above. A protein of approximately 48 kDa was weakly detected at 24 hours post-infection (h.p.i.), and accumulated to higher levels at late times after infection. This protein was not present in mock-infected cells, and was not detected with pre-immune serum. This result indicates that gp48 is a bonafide viral protein, and not a host-cell protein. Lack of antibodies in the pre-immune serum indicates that anti-gp48 antibodies are specific to the viral protein and are not cross-reactive antibodies. Synthesis of this viral protein was independent of viral DNA replication, as demonstrated by its insensitivity to phosphonoacetic acid (PAA).

The antiserum against peptide 2-1 of ORF3 also recognized the TrpE-ORF3 fusion protein made in *Escherichia coli* (*E. Coli*) from the plasmid pATH1ORF3, but not the TrpE-truncated protein. Since the TrpE-ORF3 fusion protein contains the amino acid sequence of ORF3 downstream from the AvaII site (see FIG. 1), this result confirmed that the 48 kDa viral protein is coded for by ORF3.

None of the antisera directed against ORF1 peptides 1-1 or 1-2 recognized a specific viral antigen when Western blot analysis or immunoprecipitation of $^{35}$S-cysteine or $^{35}$S-methionine labeled cells were performed.

EXAMPLE VI

Post-Translational Modifications In Vivo

The size difference between the sequence-predicted 17 kDa polypeptide discussed in Example III and the 48 kDa protein detected from infected cell lysates in Example V suggested that post-translational modifications to the 17 kDa protein had occurred in vivo. The presence of a number of potential N-linked glycosylation sites (underlined in FIG. 2) in the predicted protein further suggested that the HCMV early gene might encode an as yet-unidentified viral glycoprotein.

To test this possibility, HCMV-infected cells were radiolabeled with [$^3$H] glucosamine from 48 to 72 h p.i. The antigens were solubilized in RIPA buffer, and immunoprecipitated with antisera directed against ORF3 synthetic peptides 2-1 or 2-2. A diffuse glycoprotein band was detected by both antisera. The sizes of the immunoprecipitated glycoproteins agreed with the protein size detected by Western blot analysis. Accordingly, the 48 kDa glycoprotein product of the present HCMV early gene was designated gp48.

EXAMPLE VII

Corroboration of gp48 as an Envelope Glycoprotein Containing O- and N- linked Glycans Treatment of HCMV-infected human foreskin fibroblast cells with tunicamycin, an antibiotic which blocks N-linked glycoprotein synthesis, resulted in the accumulation of a precursor protein of 27 kDa. Since the 27 kDa precursor protein was 10 kDa larger than the 17 kDa polypeptide backbone, and the addition of O-linked oligosaccharides to nascent polypeptides was not blocked by tunicamycin, the 27 kDa precursor protein most likely contains O-linked oligosaccharides.

To determine if gp48 is a component of the envelope of the HCMV virion, extracellular viral particles of HCMV-infected human foreskin fibroblast cells were purified and subjected to Western blot analysis as described above. Antiserum against synthetic ORF3 peptide 2-1 detected a protein of 48 kDa in the infected cell lysate, and in purified virions and dense bodies. A 48 kDa protein was not detected with pre-immune serum, however. These results indicated that (i) gp48 is in the envelope of the HCMV virion, and (ii) gp48 contains N-linked glycans and possibly O-linked glycans.

EXAMPLE VIII

Vaccine Preparation

Vaccines against HCMV can be prepared which comprise gp48. The gp48 glycoprotein can be synthesized in quantity by transformation or transfection of suitable host cells (such as vaccinia or baculovirus) with the recombinant expression vectors of the present invention, or by known chemical methods of polypeptide synthesis. After isolation and purification of the glycoprotein, an immunologically-effective amount thereof is combined with a pharmaceutically-acceptable vehicle, such as a sterile liquid carrier, and parenterally administered to a mammal, in order to raise the titer of anti-HCMV antibodies in the blood of the recipient.

Vaccines against HCMV can also be prepared which comprise the 17 kDa polypeptide embodiment, p17, or the other derivatives mentioned above. The p17 polypeptide or other derivatives can be synthesized in quantity by transformation or transfection of suitable host cells with the recombinant expression vectors of the present invention, or by known chemical methods of peptide synthesis. After isolation and purification of the peptide, an immunologically-effective amount thereof is combined with a pharmaceutically-acceptable vehicle, such as a sterile liquid carrier, and parenterally administered to a human, in order to raise the titer of anti-HCMV antibodies in the blood of the recipient.

Vaccines against HCMV can also be prepared in a similar manner which comprise a subset, portion, or fragment of either gp47, p17, or the synthetic glycoproteins or peptides, respectively, derived therefrom.

For a description of a putative vaccine employing "glycoprotein A" of HCMV, see L. Pereira, U.S. Pat. No. 4,689,255, the disclosure of which is incorporated by reference herein.

Deposit of Biological Materials

Samples of the plasmid designated herein as pSPD116 (Access Code: IVI-10199) have been deposited with In Vitro International, Linthicum, Md., in accordance with the Draft PTO Deposit Policy for Biological Materials, *BNA PTCJ*, 32, 90 (1986).

The invention has been described with reference to various specific and preferred embodiments and techniques. However, it should be understood that many variations may be made while remaining within the spirit and scope of the invention.

What is claimed is:

1. An isolated and purified, immunogenic, early envelope glycoprotein of human cytomegalovirus free of any other human cytomegalovirus proteins, wherein said glycoprotein has a molecular weight of about 48,000 daltons and is encoded by an early structural gene of human cytomegalovirus, which gene maps between about 0.054 and 0.064 map units of the human cytomegalovirus genome and comprises a major open reading frame having an initiation codon located 233 base pairs downstream from the major early transcription start site of the gene.

2. A glycoprotein of claim 1 which has N- and O-linked glycosylation sites.

3. The isolated and purified human cytomegalovirus glycoprotein of claim 1, further comprising a detectable label covalently bound to the glycoprotein.

4. A monoclonal antibody which binds to the glycoprotein of claim 1.

5. A monoclonal antibody according to claim 4 which is produced by a hybridoma formed from the fusion of murine myeloma cells and spleen cells from a mouse inoculated with said glycoprotein.

* * * * *

UNITED STATES PATENT AND TRADEMARK OFFICE
CERTIFICATE OF CORRECTION

PATENT NO. : 5,180,813
DATED : January 19, 1993
INVENTOR(S) : Mark F. Stinski

It is certified that error appears in the above-identified patent and that said Letters Patent is hereby corrected as shown below:

On title page, item [54], and col. 1, line 2, "(HMCV)" should read --(HCMV)--

At column 5, line 68, after "ORF3" insert --, respectively,--.

At column 14, line 4, for "hydridoma" read --hybridoma--.

Signed and Sealed this

Twelfth Day of April, 1994

Attest:

BRUCE LEHMAN

*Commissioner of Patents and Trademarks*

*Attesting Officer*